(12) United States Patent
Wilson et al.

(10) Patent No.: US 7,128,734 B1
(45) Date of Patent: Oct. 31, 2006

(54) APPARATUS AND METHOD FOR REVERSE TUNNELING A MULTI-LUMEN CATHETER IN A PATIENT

(75) Inventors: Jon S. Wilson, Winston-Salem, NC (US); Kenneth T. Cassidy, Mocksville, NC (US); Mark C. Martel, Blues Creek, NC (US)

(73) Assignee: Arrow International, Inc., Reading, PA (US)

( * ) Notice: Subject to any disclaimer, the term of this patent is extended or adjusted under 35 U.S.C. 154(b) by 357 days.

(21) Appl. No.: 10/251,384

(22) Filed: Sep. 20, 2002

(51) Int. Cl.
| | |
|---|---|
| *A61M 31/00* | (2006.01) |
| *A61M 25/16* | (2006.01) |
| *F16D 1/00* | (2006.01) |
| *F16B 37/04* | (2006.01) |
| *B25G 3/28* | (2006.01) |

(52) U.S. Cl. .................. 604/535; 604/93.01; 403/311; 403/358; 411/182

(58) Field of Classification Search ................ 604/533, 604/534, 535, 93.01, 264, 523; 403/300, 403/309, 310, 311, 314, 358, 359.1, 361; 411/54.1, 182, 398, 512, 910
See application file for complete search history.

(56) References Cited

U.S. PATENT DOCUMENTS

| | | | |
|---|---|---|---|
| 4,134,402 A | 1/1979 | Mahurkar | 128/214 R |
| 4,299,228 A | 11/1981 | Peters | 604/122 |
| 4,327,722 A | 5/1982 | Groshong | 604/510 |
| 4,432,752 A | 2/1984 | Marlon | 604/500 |
| 4,453,928 A | 6/1984 | Steiger | 604/500 |
| RE31,873 E | 4/1985 | Howes | 128/674 |
| 4,543,087 A | 9/1985 | Sommercorn et al. | 604/43 |
| 4,568,329 A | 2/1986 | Mahurkar | 604/43 |

(Continued)

FOREIGN PATENT DOCUMENTS

WO    WO 9722374    6/1997

OTHER PUBLICATIONS

Instructions for Use (Copyright Dated 1990) for Polycath Polyurethane Central Venous Catheter; believed to have been packaged with product believed to have been sold in the United States before Jan. 2000 and related marketing materials.

(Continued)

*Primary Examiner*—Kevin Sirmons
*Assistant Examiner*—Mark K Han
(74) *Attorney, Agent, or Firm*—Amster, Rothstein & Ebenstein, LLP

(57) ABSTRACT

An apparatus and method for tunneling a distal portion of a multilumen catheter tube in a patient is disclosed. The apparatus includes a connector having a distal end and a proximal end. The proximal end includes a first coupling portion for selective connection to a distal end of the multilumen catheter tube, and the distal end of the connector includes a second coupling portion. A trocar is provided having a first end and a second end. The second end of the trocar is configured for selective connection to the coupling portion of the connector. The connector and the second end of trocar are configured such that they are substantially coaxially aligned with the multilumen catheter tube when the first coupling portion of the connector is selectively joined with the distal end of the multilumen catheter tube and the second end of the trocar is selectively engaged with the second coupling portion of the connector. A method of reverse tunneling a multilumen catheter tube using such an apparatus is also disclosed.

27 Claims, 8 Drawing Sheets

U.S. PATENT DOCUMENTS

| | | |
|---|---|---|
| 4,619,643 A | 10/1986 | Bai |
| 4,623,327 A | 11/1986 | Mahurkar ............... 604/4 |
| 4,643,711 A | 2/1987 | Bates ..................... 604/4 |
| 4,675,004 A | 6/1987 | Hadford et al. .......... 604/44 |
| 4,681,122 A | 7/1987 | Winters et al. .......... 128/736 |
| 4,682,978 A | 7/1987 | Martin .................... 604/43 |
| 4,692,141 A | 9/1987 | Mahurkar ................ 604/43 |
| 4,772,268 A | 9/1988 | Bates ..................... 604/43 |
| 4,772,269 A | 9/1988 | Twardowski ............ 604/175 |
| 4,808,155 A | 2/1989 | Mahurkar ................ 604/174 |
| 4,832,687 A | 5/1989 | Smith, III ................ 604/506 |
| 4,895,561 A | 1/1990 | Mahurkar ................ 604/43 |
| 5,053,003 A | 10/1991 | Dadson et al. ........... 604/28 |
| 5,053,004 A | 10/1991 | Markel et al. ............ 604/43 |
| 5,053,023 A | 10/1991 | Martin .................... 604/27 |
| 5,059,170 A | 10/1991 | Cameron ................. 604/43 |
| 5,106,368 A | 4/1992 | Uldall et al. ............. 604/43 |
| 5,129,891 A | 7/1992 | Young .................... 604/283 |
| 5,171,227 A | 12/1992 | Twardowski ............ 604/175 |
| 5,190,520 A | 3/1993 | Fenton, Jr. et al. ...... 604/29 |
| 5,312,337 A | 5/1994 | Flaherty et al. .......... 604/93 |
| 5,334,185 A | 8/1994 | Giesy et al. |
| 5,342,386 A | 8/1994 | Trotta .................... 606/194 |
| 5,360,397 A | 11/1994 | Pinchuk .................. 604/27 |
| 5,380,276 A | 1/1995 | Miller et al. ............. 604/28 |
| 5,399,168 A | 3/1995 | Wadsworth, Jr. et al. ... 604/175 |
| 5,417,668 A | 5/1995 | Setzer et al. ............. 604/263 |
| 5,423,768 A | 6/1995 | Folder .................... 604/200 |
| 5,431,661 A | 7/1995 | Koch ..................... 606/108 |
| 5,472,432 A | 12/1995 | Martin .................... 604/248 |
| 5,509,897 A | 4/1996 | Twardowski et al. ..... 604/43 |
| 5,558,635 A | 9/1996 | Cannon ................... 604/49 |
| 5,599,328 A | 2/1997 | Stevens .................. 604/280 |
| 5,624,413 A | 4/1997 | Markel et al. ............ 604/280 |
| 5,632,729 A | 5/1997 | Cai et al. ................. 604/93 |
| 5,637,102 A | 6/1997 | Tolkoff et al. ........... 604/49 |
| 5,685,867 A | 11/1997 | Twardowski ............ 604/523 |
| 5,704,915 A | 1/1998 | Melsky et al. ........... 604/175 |
| 5,718,678 A | 2/1998 | Fleming, III ............ 604/43 |
| 5,743,873 A | 4/1998 | Cai et al. ................. 604/93 |
| 5,772,643 A | 6/1998 | Howell et al. ............ 604/283 |
| 5,776,111 A | 7/1998 | Tesio ..................... 604/43 |
| 5,797,869 A | 8/1998 | Martin et al. ............ 604/43 |
| 5,807,311 A | 9/1998 | Palestrant ............... 604/28 |
| 5,876,366 A | 3/1999 | Dykstra et al. |
| 5,944,732 A | 8/1999 | Raulerson et al. ....... 606/167 |
| 5,947,953 A | 9/1999 | Ash et al. ................ 604/508 |
| 5,989,206 A | 11/1999 | Prosl et al. .............. 604/501 |
| 5,989,213 A | 11/1999 | Maginot .................. 604/28 |
| 6,001,079 A | 12/1999 | Pourchez |
| 6,033,382 A | 3/2000 | Basta ..................... 604/104 |
| 6,074,374 A | 6/2000 | Fulton .................... 304/249 |
| 6,086,555 A | 7/2000 | Eliasen et al. ........... 604/93 |
| 6,113,572 A | 9/2000 | Gailey et al. ............ 604/93 |
| 6,156,016 A | 12/2000 | Maginot .................. 604/264 |
| 6,190,349 B1 | 2/2001 | Ash et al. ................ 604/43 |
| 6,190,371 B1 | 2/2001 | Maginot et al. .......... 604/523 |
| 6,206,849 B1 | 3/2001 | Martin et al. ............ 604/43 |
| 6,293,927 B1 | 9/2001 | McGuckin, Jr. .......... 604/266 |
| 6,342,120 B1 | 1/2002 | Basta ..................... 156/242 |
| 6,428,513 B1 | 8/2002 | Abrahamson ............ 604/174 |
| 6,453,185 B1 * | 9/2002 | O'Keefe .................. 600/378 |
| 6,585,705 B1 | 7/2003 | Maginot et al. .......... 604/265 |
| 6,638,242 B1 | 10/2003 | Wilson et al. |
| 6,682,498 B1 | 1/2004 | Ross |
| 6,682,519 B1 | 1/2004 | Schon .................... 604/508 |
| 6,749,574 B1 | 6/2004 | O'Keefe |
| 2001/0041857 A1 | 11/2001 | Sansoucy ............... 604/33 |
| 2003/0088213 A1 | 5/2003 | Schweikert et al. ...... 604/177 |
| 2003/0153898 A1 | 8/2003 | Schon et al. ............ 604/544 |

OTHER PUBLICATIONS

Instructions for Use (Copyright Dated 1992) for FloLock Single Lumen Bi-directional Valved Catheter ; believed to have been packaged with product believed to have been sold in the United States before Jan. 2000.

Instructions for Use (not dated) for Infuse-a-Cath Polyurethane Central Venous Catheter; believed to have been packaged with product believed to have been sold in the United States before Jan. 2000.

Pictures of device believed to be partial sample of a product believed to have been sold in the United States before Jan. 2000 with the Polycath and/or Infuse-a-Cath Instructions for Use.

Copending U.S. Appl. No. 10/251,411; entitled Multi-Lumen Catheter with Attacheble Hub, filed Sep. 20, 2002.

Copending U.S. Appl. No. 10/231,577; entitled Multi-Lumen Catheter with Integrated Connector, filed Aug. 30, 2002.

Copending U.S. Appl. No. 10/231,748; Double Y-Shaped Multi-Lumen Catheter With Selectively Attachable Hubs, filed Aug. 30, 2002.

Copending U.S. Appl. No. 10/612,532; entitled Multi-Lumen Catheter with Attachable Hub, filed Jul. 1, 2003.

Abandoned U.S. Appl. No. 10/086,033; entitled Multi-Lumen Catheter with Attachable Hub, filed Jan. 24, 2001.

Instructions For Use For Diatek Cannon Catheter Product First Sold in the United States Sep. 2001.

Believed to be an unpublished sketch of a conception by Dr. John Frusha; date of sketch believed to be Jun. 24, 1997.

* cited by examiner

APPARATUS AND METHOD FOR REVERSE TUNNELING A MULTI-LUMEN CATHETER IN A PATIENT

FIELD OF THE INVENTION

The present invention relates generally to medical instrumentation and more specifically to an apparatus and method for subcutaneously tunneling a multilumen catheter in a patient.

BACKGROUND

Catheters, generally, are hollow, flexible tubes for insertion into a body cavity, duct, or vessel to allow the passage of fluids or distend a passageway. Catheters are often used for temporary or long-term dialysis treatment. Dialysis treatment provides for blood to be withdrawn from the patient, purified, and then returned to the patient. Thus, in dialysis treatment, catheters are used to allow passage of a patient's blood into and out of the patient's body. For optimal performance during dialysis treatment, the catheter tips, both in-flow and out-flow, should be placed in close proximity to the heart. Typically, medical personnel use either a double lumen catheter or two single lumen catheters. Both types, however, present certain deficiencies.

While double lumen catheters (e.g., U.S. Pat. No. 4,895,561) allow for a single venous insertion of the catheter into the desired vein, double lumen catheters typically do not provide for accuracy of catheter tip placement. Due to differences among patients, optimal tip position varies from patient to patient. Non-optimal tip position may significantly lower flow values, resulting in less effective dialysis treatment. For current double lumen catheters, a physician must make an estimate regarding the appropriate catheter tube length prior to beginning the procedure of catheterization. Then, a subcutaneous tunnel is made from the preferred end position of the hub assembly, namely, away from the neck of the patient in order to allow for more convenient access to the dialysis treatment equipment. The double lumen catheter tube is then tunneled forwardly into the patient's vein. The initial estimate and subsequent forward tunneling may result in less than optimal tip placement.

With the use of two independent catheters (e.g., U.S. Pat. Nos. 5,776,111 and 5,624,413) the problem of tip placement is addressed. The hub assembly of each catheter is removable from the tube and tip portion of the catheter, thereby allowing the catheter tip to be placed directly into the vein and advanced into the desired position. Then, the proximal end of the catheter can be reverse tunneled and trimmed to a desired length. Thereafter, the hub assembly is attached. Deficiencies, however, exist in this method of catheterization as well. One problem associated with this method is that it requires two separate venous insertions, namely, two tunnels and two of each accessory instruments used for the procedure. Therefore, there is increased surgical time required to place two catheters, there are two wound entry sites which doubles the risk of post-surgical infection, and the two catheters together are significantly larger in diameter than one double lumen catheter.

Therefore, there is a need for an apparatus and method that permits accurate tip placement of a multilumen catheter, and also permits and facilitates subcutaneous reverse tunneling of the multilumen catheter tube after tip placement.

SUMMARY OF THE INVENTION

An apparatus and method are provided for reverse tunneling a distal portion of a multilumen catheter tube. The apparatus and method are particularly adapted for use with a multilumen catheter having a selectively detachable hub assembly like that disclosed in applicant's pending application Ser. No. 09/769,052, filed Jan. 24, 2001, and pending application Ser. No. 10/086,033, the contents of which are incorporated herein by reference. The apparatus and method permit the proximal tips of a multilumen catheter to be accurately positioned within a patient's vein prior to subcutaneous tunneling of the distal portion of the catheter tube, and permit the distal end of the catheter tube to be subcutaneously tunneled in the patient prior to attachment to a hub assembly.

An apparatus is disclosed for tunneling a distal portion of a multilumen catheter tube in a patient. In one embodiment, the apparatus includes a connector having a proximal end. The proximal end of the connector includes a first coupling portion configured for selective connection to a distal end of the multilumen catheter tube. An opposed distal end of the connector includes a second coupling portion. A trocar is provided having a first end and a second end. The second end of the trocar is configured for selective connection to the coupling portion of the connector. The connector and the second end of trocar are configured such that they are substantially coaxially aligned with the multilumen catheter tube when the first coupling portion of the connector is selectively joined with the distal end of the multilumen catheter tube and the second end of the trocar is selectively engaged with the second coupling portion of the connector. The trocar can be used to form a subcutaneous tunnel in a patient. The connector and trocar can then be used to guide the distal portion of the multilumen catheter tube through the subcutaneous tunnel after the catheter tips on the proximal end of the multilumen catheter tube have been accurately positioned in the patient.

In one embodiment, the trocar includes an elongated shaft having a substantially pointed insertion end and a substantially circumferential groove in the shaft proximate to the insertion end. The groove can be used to connect the insertion end of the trocar to the connector. The trocar may also include a handle end opposite from the insertion end.

A selectively attachable connector is disclosed for use in subcutaneously tunneling a multilumen catheter tube in a patient. In one embodiment, the connector includes a body having a first end and a second end. An opening is provided in the first end of the body, and a coupling portion is positioned inside the opening. A plurality of prongs are provided on the second end of the body. Each prong is configured for secure engagement within a single lumen in an end of the multilumen catheter tube.

A method of subcutaneously reverse tunneling a multilumen catheter tube in a patient is also disclosed. In one embodiment, the method includes forming a first incision in the skin of a patient and forming a second incision that is remote from the first. A subcutaneous tunnel is then formed between the first and second incisions by inserting a trocar into one of the incisions and passing the trocar subcutaneously until a tip of the trocar outwardly extends from the other incision. A selectively attachable connector is attached to a first end of the multilumen catheter tube such that the connector is substantially coaxially aligned with the multilumen catheter tube. The tip of the trocar is then attached to the connector such that the trocar, connector, and multilumen catheter tube are substantially coaxially aligned with each other. A portion of the catheter tube is drawn into and through the subcutaneous tunnel by pulling the trocar and the attached connector and first end of the multilumen catheter tube through the tunnel.

These and other aspects of the present invention as disclosed herein will become apparent to those skilled in the art after a reading of the following description of the preferred embodiments and drawings. The description and drawings are for the purpose of describing a preferred embodiment of the invention and are not intended to limit the present invention.

DETAILED DESCRIPTION

For the purposes of the following description and the claims appended hereto, the relative term "proximal" refers to those portions of a catheter and those portions of components of the catheter which are nearest the insertion end of the catheter, that is, the end of the catheter that is inserted into an area of a patient's body being catheterized, such as a blood vessel. Conversely, the relative term "distal" refers to those portions of a catheter and those portions of components of the catheter which are farthest from the insertion end of the catheter.

Figure 1:
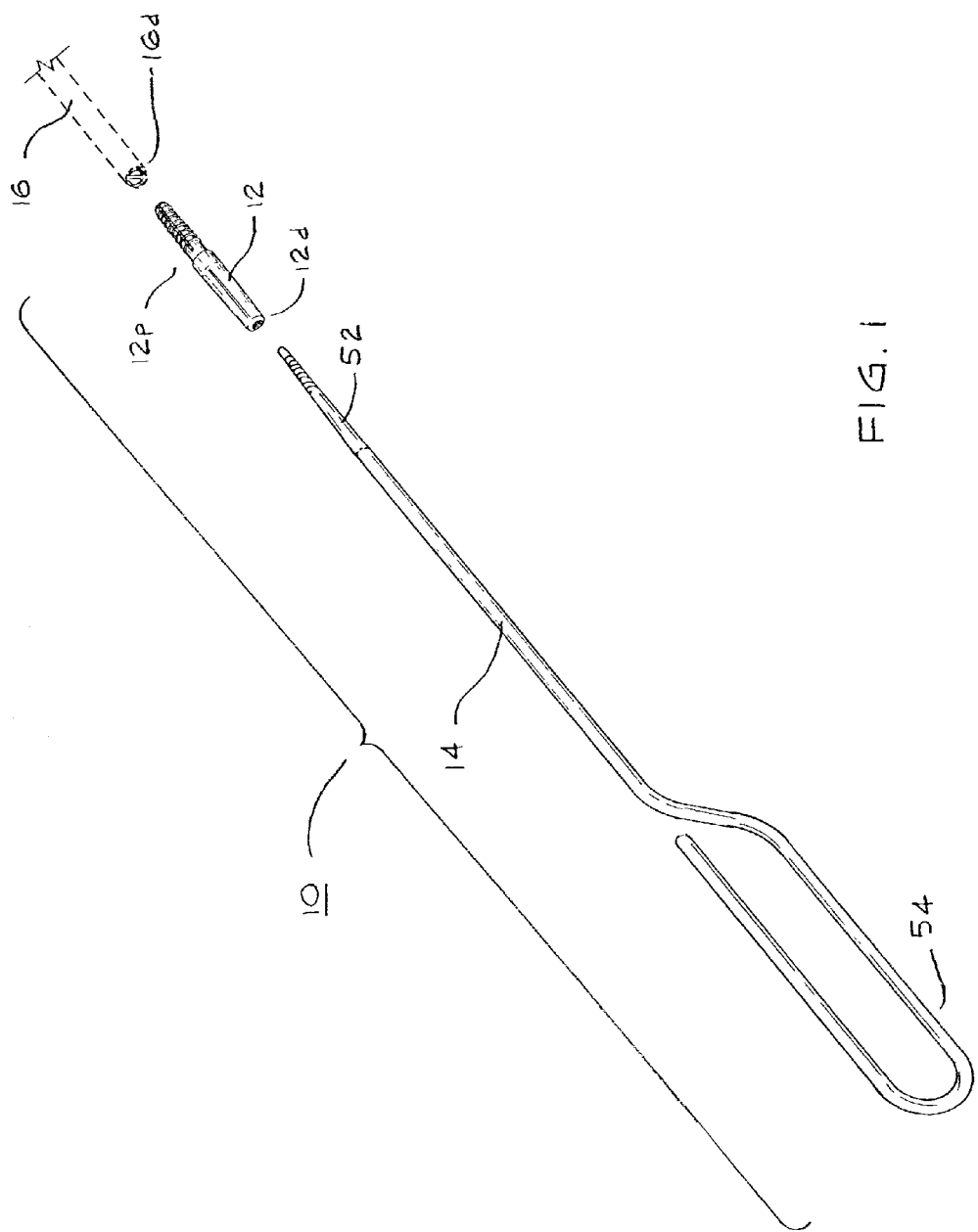
FIG. 1 is a perspective view of an apparatus according to the present invention.

As shown the Figures, an apparatus 10 is provided for reverse tunneling a multilumen catheter 16 in a patient. In the embodiment shown in FIG. 1, the apparatus 10 includes a connector 12 and a trocar 14. The connector 12 includes a proximal end 12p that is configured for selective connection to the distal end 16d of a multilumen catheter tube 16. The connector 12 also includes a distal end 12d that is configured for selective connection to an insertion end 52 of the trocar 14. As shown in FIG. 1, the trocar 14, connector 12, and multilumen catheter tube 16 are substantially coaxially aligned with each other when connected together. The trocar 14 and connector 12 combine to provide a tool for guiding the distal end 16d of the multilumen catheter tube through a subcutaneous tunnel as described in detail below.

Figure 2:
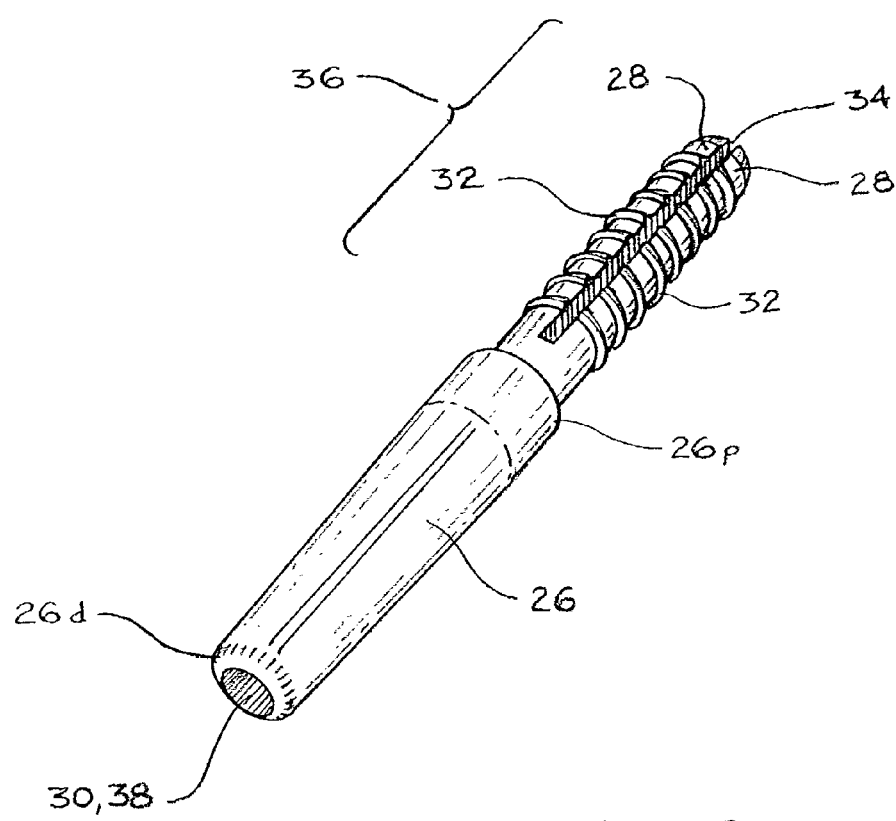
FIG. 2 is a perspective view of a connector for use in the apparatus of FIG. 1.
Figure 3:
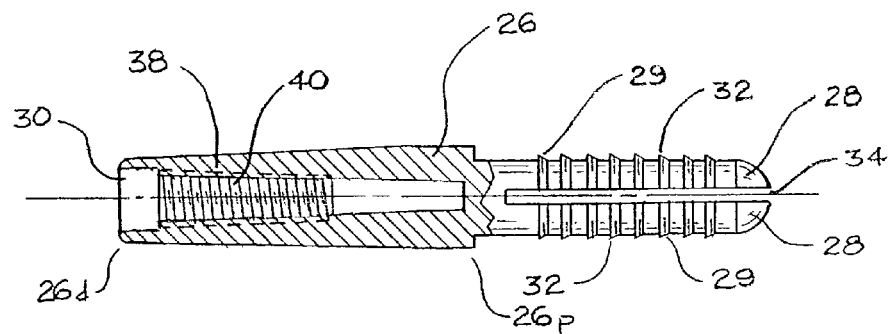
FIG. 3 is a cross-sectional view of one embodiment of the connector of FIG. 2.
Figure 4:
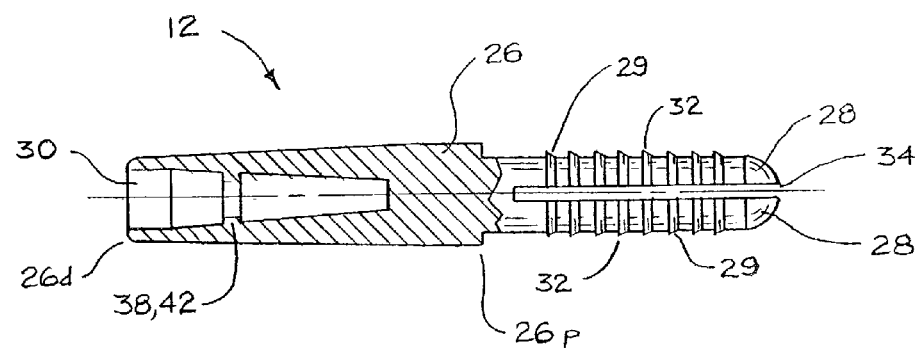
FIG. 4 is a cross-sectional view of an alternative embodiment of the connector shown in FIG. 2.

FIGS. 2–4 show various embodiments of the connector 12. In the embodiment shown in FIGS. 2 and 3, the connector 12 includes a body 26 having a distal end 26d and a proximal end 26p. The body 12 may have a substantially cylindrical or substantially frustoconical outer shape as shown. A plurality of substantially parallel prongs 28 are connected to the proximal end 26p of the connector body 26.

Figure 7:
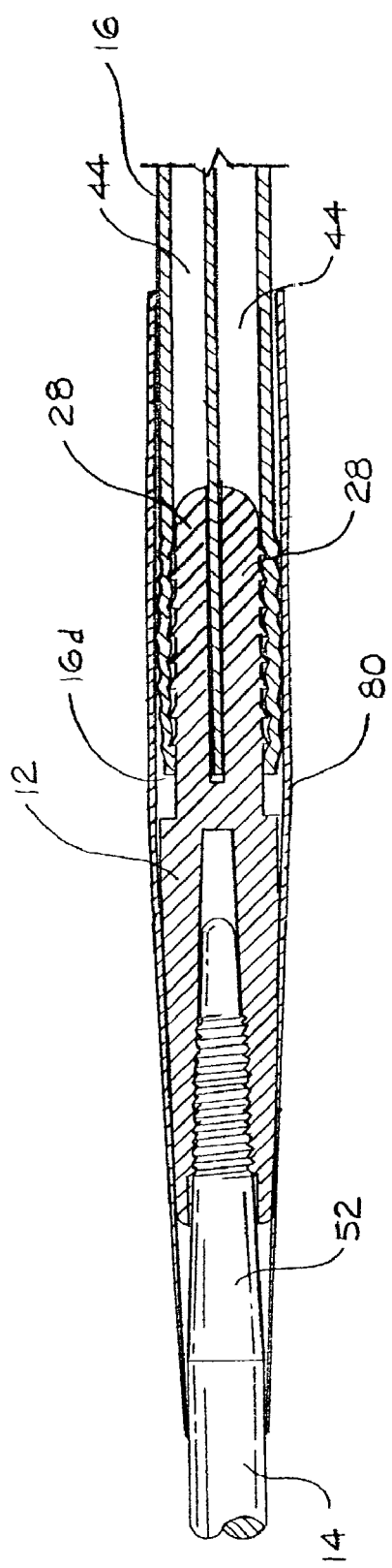
FIG. 7 is a cross-sectional view of an alternative embodiment of the apparatus shown in FIG. 1.

In this embodiment, the prongs 28 provide a first coupling portion 36 for selectively joining the connector 12 to the distal end 16d of a multilumen catheter tube 16 as shown in FIG. 1. Each of the plurality of prongs 28 are configured to be inserted into a single lumen 44 at the end 16d of a multilumen catheter tube 16 as shown in FIG. 7, thereby connecting the connector 12 and multilumen catheter tube 16 such that they are substantially coaxially aligned with each other. The prongs 28 have cross sectional shapes which substantially match the cross-sectional shape of the lumens 44 in the catheter tube 16. For example, for a typical dual-lumen catheter tube, the lumens typically are D-shaped. Accordingly, the prongs 28 of a connector 12 designed for use with a conventional dual-lumen catheter may have matching D-shaped cross-sections. The plurality of prongs 28 may be separated by one or more slits 34 as shown in FIG. 3. The prongs 28 may be sized to be at least slightly larger than the corresponding lumens 44 in the catheter tube 16 such that insertion of the prongs 28 into the lumens 44 creates a tight, frictional fit.

Outer surfaces of the prongs 28 of the connector 12 may include a plurality of ribs or barbs 32 as shown in FIGS. 2 and 3. The ribs or barbs 32 may include a tapered leading edge 29 as shown in FIG. 3 to facilitate insertion of the prongs 28 into the lumens 44 of the catheter tube 16. The saw tooth shape of the ribs or barbs 32 as shown in FIG. 2 acts to resist extraction of the prongs 28 from the lumens 44 of the catheter tube 16 after the prongs 28 are inserted into the lumens 44. The prongs 28 may also have other cross-sectional shapes and other outer surface configurations and finishes that provide a sufficient frictional engagement between the prongs 28 and the lumens 44 of the catheter tube 16. Because the frictional engagement between the prongs 28 and the lumens 44 of multilumen catheter tube 16 is sufficient to maintain the connection during tunneling of the catheter tube 16, it is unnecessary to use an adhesive for the attachment.

Figure 5:
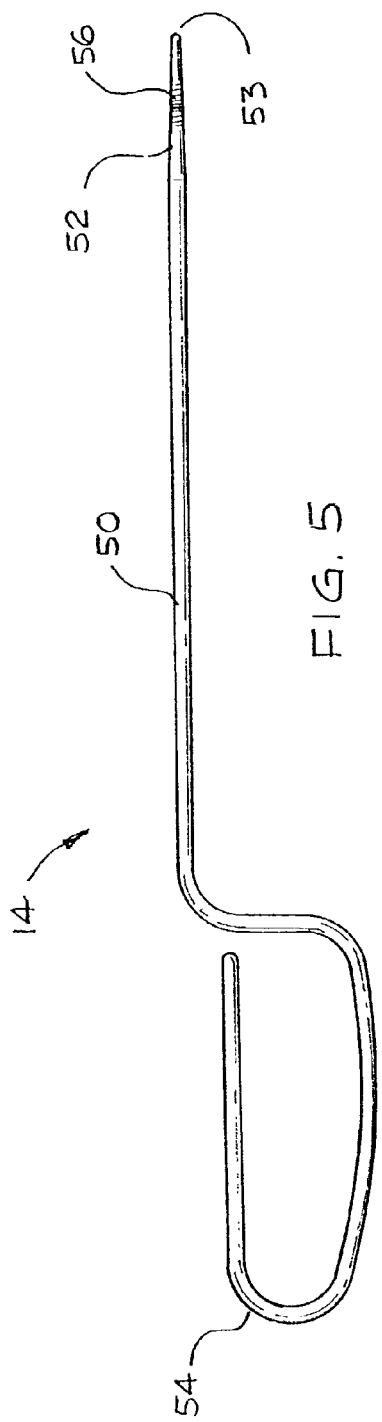
FIG. 5 is an elevation view of the trocar shown in FIG. 1 for use with the embodiment of the connector shown in FIGS. 2 and 3.

In the embodiment of the connector 12 shown in FIG. 3, the distal end of the connector body 26 includes an opening or bore 30. A second coupling portion 38 is provided inside the opening 30. In the embodiment shown in FIG. 3, the coupling portion includes a plurality of internal threads 40. The internal threads 40 are sized for mating engagement with corresponding external threads 56 on a trocar 14 as shown in FIG. 5 and as described below. The internal threads 40 may be tapered as shown in FIG. 3. In an alternative arrangement shown in FIG. 4, the coupling portion 38 may include a collar 42 disposed in the opening or bore 30. The collar 42 is sized and shaped for gripping engagement with a mating groove 58 in a trocar 14 as shown in FIG. 6 and as described below.

The connector 12 may be constructed of plastic, metal, polyvinyl chloride, or any other suitable material. Preferably, the material is sufficiently rigid to maintain the engagement between the coupling portions 36, 38 of the connector 12 and the catheter tube 16 and the trocar 14 when the connector 12 is used to tunnel a multilumen catheter tube as described in detail below. Also, the material is preferably sufficiently tough to resist cracking and breaking during use.

As shown in FIG. 1, a trocar 14 is provided for use with a connector 12 like that described above. One embodiment of the trocar 14 is shown in FIG. 5. The trocar 14 includes an elongated shaft 50 including an insertion end 52 and a handle end 54. The insertion end 52 culminates in an insertion tip 53. The tip 53 is preferably substantially pointed so that the trocar 14 can be used to form a subcutaneous tunnel in a patient as described more fully below.

Figure 6:
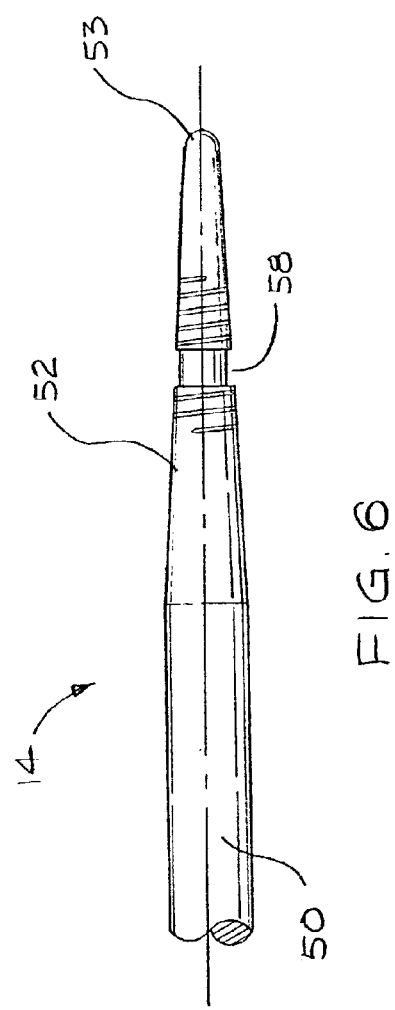
FIG. 6 is a partial elevation view of an alternative embodiment of the trocar shown in FIG. 1 for use with the embodiment of the connector shown in FIGS. 2 and 4.

The insertion tip 53 may, however, be slightly rounded as shown in FIGS. 5 and 6. The insertion end 52 is configured for connection to the second coupling portion 38 of the connector 12. In the embodiment of the trocar 14 shown in FIG. 5, the insertion end 52 is substantially tapered and includes a plurality of external threads 56. The external threads are sized for mating engagement with the internal threads of the embodiment of the connector 12 shown in FIG. 3 and described above.

An alternative embodiment of the trocar is shown in FIG. 6. In this embodiment, the tapered insertion end 52 of the trocar 14 includes a circumferential groove 58. The groove 58 is sized and shaped for mating engagement with the collar 42 of the connector 12 as shown in FIG. 4 and described above. In this arrangement, the insertion tip of the trocar is inserted into the opening or bore 30 at the distal end 12d of the connector 12 until the collar 42 snaps into the groove 58, thereby connecting the trocar 14 to the connector 12. The tapered end of the trocar 14 acts to spread the collar 42 as the trocar is inserted into the opening 30 and until the collar 42 snaps into the groove 58.

In order to provide a smooth outer contour to the interconnected trocar 14, connector 12 and catheter tube 16 that will facilitate passage of the assembled components through a subcutaneous tunnel, an outer sheath 80 may be provided as shown in FIG. 7. The sheath 80 has a substantially tubular shape, and preferably includes a tapered outer surface proximate to its distal end 80d. Preferably, the distal end 80d of the sheath 80 is sized and shaped so that it forms a smooth transition at its intersection with the insertion end 52 of the trocar 14. Preferably, the sheath 80 has a smooth outer surface texture to facilitate passage of the sheath 80 through a subcutaneous tunnel.

Figure 8A:
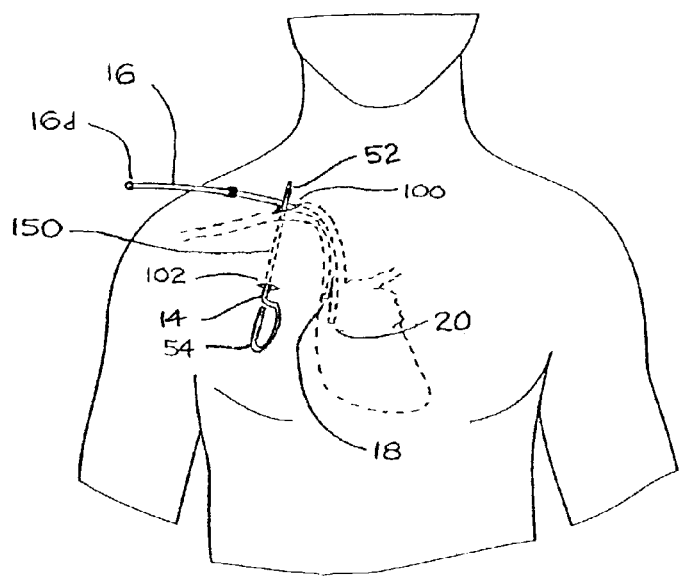
FIGS. 8A–8D illustrate a method for subcutaneously tunneling a distal portion of a multilumen catheter tube in a patient using an apparatus like that shown in FIGS. 1–7.

A tunneling apparatus like that described above may be used in a method for tunneling a distal portion of multilumen catheter tube in a patient after the proximal tips of the catheter have been accurately placed in the patient. A preferred method for inserting the proximal tips of a multilumen catheter with a selectively attachable hub is described in co-pending application Ser. No. 09/769,052, filed Jan. 24, 2001, at page 8, line 11, to page 10, line 3. After such insertion of the proximal tips, the distal end 16d of the multi-lumen catheter tube 16 protrudes from the patient through a first incision 100 as shown in FIG. 8A. At this point in the catheterization procedure, the distal end 16d of the catheter tube 16 is ready to be subcutaneously tunneled in the patient. A method of tunneling a catheter tube as described herein may be referred to as "reverse tunneling" because distal portions of the multilumen catheter tube are tunneled in a direction that is opposite from the direction of insertion of the proximal portions of the catheter into the patient.

A tunnel of about 8 to 10 cm in length is created by means of the trocar 14 as depicted in FIG. 8A. A second incision 102 is made in the patients skin remote from the first incision 100 in a caudal and internal direction. A subcutaneous tunnel is then formed by inserting the insertion end 52 of the trocar 14 into the second incision 102 and passing the trocar 14 subcutaneously until the insertion end 52 protrudes outwardly from the first incision 100 as shown in FIG. 8A.

Figure 8B:
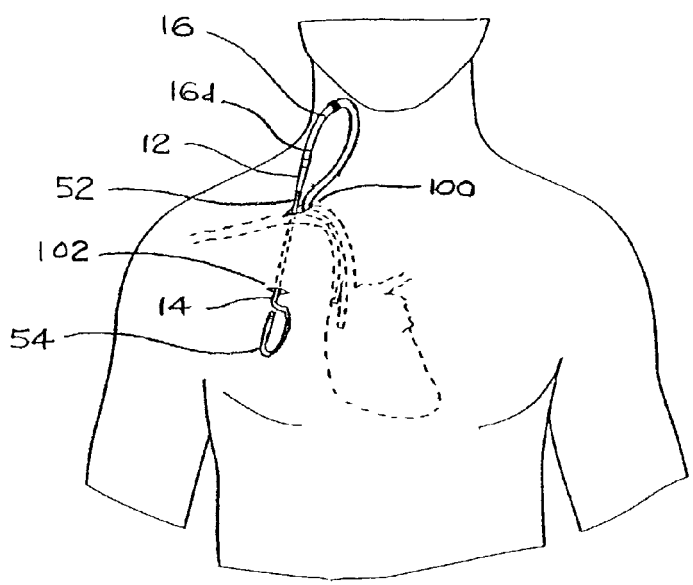
Figure 8C:
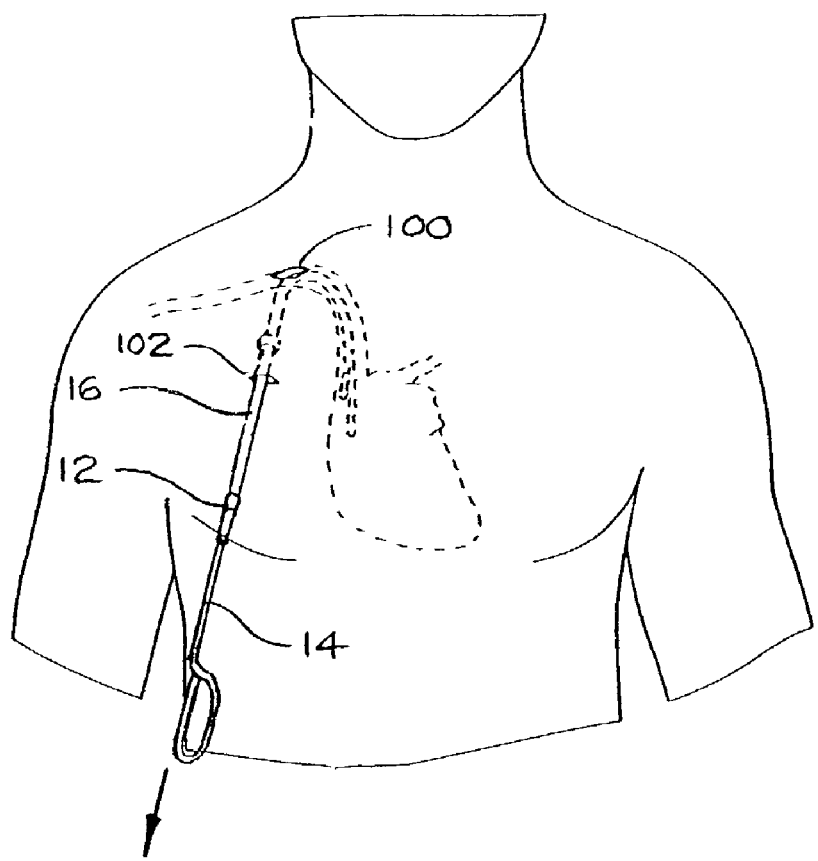
Figure 8D:
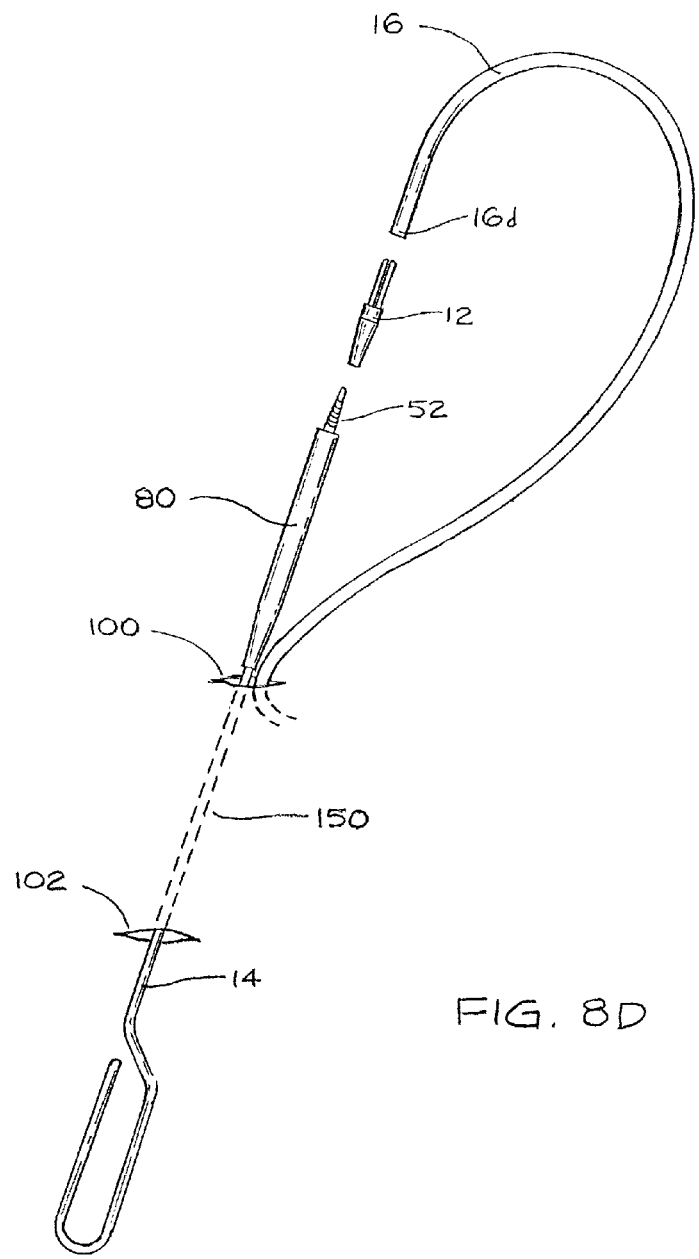

Referring to FIG. 8B, a connector 12 is selectively attached to the distal end 16d of the multilumen catheter tube 16, and the protruding insertion end 52 of the trocar 14 is attached to the connector 12. Using the handle end 54 of the trocar 14, the connector 12 and attached distal end of the catheter tube 16 are gently pulled through the tunnel until the loop shown in FIG. 8B is gone as shown in FIG. 8C. When correctly inserted, the catheter tube 16 rests over the clavicle of the patient. Finally, once the catheter tube 16 is in a proper final position, the connector 12 and a portion of the distal end 16d of the catheter tube 16 protruding from the second incision 102 may be severed from the remainder of the catheter tube 16 (not shown).

In order to provide a smooth outer profile to the connection, a sheath 80 may placed over a portion of the insertion end 52 of the trocar 14, the connector 12, and a portion of distal end 16d of the catheter tube 16. In a preferred method, the sheath 80 is back-fit over the trocar 14 before connection is made between the trocar 14 and the connector 12. After the insertion end of the trocar is attached to the connector 12 and the distal end 16d of the multilumen catheter tube 16 is connected to the connector 12, the outer sheath 80 is assembled as shown in FIG. 7. The distal end 16d of the catheter 16 is then pulled through the subcutaneous tunnel 150 as described above, and the sheath 80 and connector 12 are removed from the catheter tube 16.

Once the reverse tunneling of the catheter tube 16 is complete, the distal end 16d of the catheter tube 16 can then be connected to a fluid exchange device.

Although specific embodiments of the present invention have been illustrated and described in detail, it is to be expressly understood that the invention is not limited thereto. The above detailed description of the embodiment is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. An apparatus for tunneling a distal portion of a multilumen catheter in a patient, the apparatus comprising:
   (a) a connector having a distal end and a proximal end, the proximal end comprising a first coupling portion having a plurality of prongs, each of the plurality of prongs being configured to be selectively inserted into a single lumen at a distal end of the multilumen catheter, and the distal end of the connector comprising a second coupling portion; and
   (b) a trocar having a first end and a second end, the second end being configured for selective connection to the second coupling portion of the connector;
   wherein the connector and the second end of trocar are configured such that they are substantially coaxially aligned with the multilumen catheter when the first coupling portion of the connector is selectively joined with the distal end of the multilumen catheter and the second end of the trocar is selectively engaged with the second coupling portion of the connector.

2. An apparatus according to claim 1 wherein the connector has a largest outer diameter that is substantially equal to an outer diameter of the multilumen catheter tube.

3. An apparatus according to claim 1 wherein a portion of the connector proximate to its distal end has a substantially cylindrical or substantially frustoconical outer shape.

4. An apparatus according to claim 1 wherein the second end of the trocar comprising a rounded insertion tip.

5. An apparatus according to claim 1 wherein each of the plurality of prongs includes at least one rib or barb being designed to substantially resist withdrawal of the prongs from the lumens of the multilumen catheter tube after insertion of the prongs into the lumens.

6. An apparatus according to claim 1 wherein each of the plurality of prongs includes a plurality of spaced ribs or barbs.

7. An apparatus according to claim 1 wherein the trocar includes a tapered outer surface proximate to the second end, the tapered outer surface substantially culminating in a point at the second end of the trocar.

8. An apparatus according to claim 1 wherein the trocar further comprises a plurality of external threads proximate to the second end, and the coupling portion of the connector comprises a bore in the distal end of the connector, wherein the threads and bore are configured for selective threaded engagement with each other.

9. An apparatus according to claim 1 wherein the first end of the trocar comprises a handle.

10. An apparatus according to claim 1 wherein:
 (a) the coupling portion of the connector comprises a collar in a bore in the distal end of the connector; and
 (b) the trocar includes a circumferential groove substantially proximate to the second end;
 wherein the collar is configured to engage in the groove when the second end of the trocar is inserted into the bore, thereby selectively connecting the trocar to the connector.

11. An apparatus according to claim 1 further comprising a sheath, the sheath having a substantially smooth outer profile and being configured to substantially cover at least a portion of the trocar, the connector when connected to the trocar, and at least a portion of the distal end of the multilumen catheter tube when connected to the connector.

12. An apparatus for tunneling a distal portion of a multilumen catheter in a patient, the apparatus comprising:
 (a) a connector having a distal end and a proximal end, the proximal end comprising a first coupling portion configured for selective connection to a distal end of the multilumen catheter tube, and the distal end of the connector comprising a second coupling portion, the second coupling portion of the connector comprises a collar in a bore in the distal end of the connector; and
 (b) a trocar having a first end and a second end, the second end being configured for selective connection to the second coupling portion of the connector and includes a circumferential groove substantially proximate to the second end, wherein the collar is configured to engage in the groove when the second end of the trocar is inserted into the bore, thereby selectively connecting the trocar to the connector;
 wherein the connector and the second end of trocar are configured such that they are substantially coaxially aligned with the multilumen catheter when the first coupling portion of the connector is selectively joined with the distal end of the multilumen catheter and the second end of the trocar is selectively engaged with the second coupling portion of the connector.

13. An apparatus according to claim 12 wherein the trocar includes a tapered outer surface proximate to the second end, the tapered outer surface substantially culminating in a point at the second end of the trocar.

14. An apparatus according to claim 12 wherein the trocar further comprises a plurality of external threads proximate to the second end, and the coupling portion of the connector comprises a bore in the distal end of the connector, wherein the threads and bore are configured for selective threaded engagement with each other.

15. An apparatus according to claim 12 wherein the first end of the trocar comprises a handle.

16. An apparatus according to claim 12 wherein the connector has a largest outer diameter that is substantially equal to an outer diameter of the multilumen catheter tube.

17. An apparatus according to claim 12 wherein a portion of the connector proximate to it is distal end has a substantially cylindrical or substantially frustoconical outer shape.

18. An apparatus for tunneling a distal portion of a multilumen catheter in a patient, the apparatus comprising:
 (a) a connector having a distal end and a proximal end, the proximal end comprising a first coupling portion comprising a plurality of prongs, each of the plurality of prongs being configured to be inserted into a single lumen at a distal end of the multilumen catheter; and
 (b) a trocar having a first end and a second end, the second end coupled to the distal end of the connector;
 wherein the connector and the second end of trocar are configured such that they are substantially coaxially aligned with the multilumen catheter.

19. An apparatus according to claim 18 wherein the connector has a largest cross-sectional profile that is substantially equal to a largest cross-sectional profile of the multilumen catheter tube.

20. An apparatus according to claim 18 wherein the trocar further comprises a rounded insertion tip.

21. An apparatus according to claim 18 wherein the trocar includes a tapered outer surface proximate to the rounded insertion tip, the tapered outer surface substantially culminating in the rounded insertion tip.

22. An apparatus according to claim 18 further comprising a sheath, the sheath having a substantially smooth outer profile and being configured to substantially cover at least a portion of the trocar, the connector, and at least a portion of the distal ends of the single lumens of the multilumen catheter when connected to the connector.

23. An apparatus for tunneling a distal portion of a multilumen catheter in a patient, the apparatus comprising:
 (a) a connector having a distal end and a proximal end, the proximal end comprising a first coupling portion comprising a plurality of prongs, each of the plurality of prongs are inserted into a single lumen at a distal end of the multilumen catheter; and
 (b) a trocar having a first end and a second end, the second end being selectively coupled to the distal end of the connector;
 wherein the connector and the second end of trocar are configured such that they are substantially coaxially aligned with the multilumen catheter when the second end of the trocar is coupled to the distal end of the connector.

24. An apparatus according to claim 23 wherein the trocar further comprises a rounded insertion tip.

25. An apparatus according to claim 23 wherein the trocar includes a tapered outer surface proximate to the rounded insertion tip, the tapered outer surface substantially culminating in the rounded insertion tip.

26. An apparatus according to claim 23 further comprising a sheath, the sheath having a substantially smooth outer profile and being configured to substantially cover at least a portion of the trocar, the connector, and at least a portion of the distal ends of the single lumens of the multilumen catheter when connected to the connector.

27. An apparatus according to claim 23 wherein the trocar further comprises an engaging surface proximate to the second end of the trocar, wherein the engaging surface engages the distal end of the connector.

* * * * *